United States Patent
Di Santo et al.

(10) Patent No.: US 12,429,472 B2
(45) Date of Patent: Sep. 30, 2025

(54) METHODS AND SYSTEMS FOR PREDICTING FORMATION THERMAL PROPERTIES

(71) Applicants: Schlumberger Technology Corporation, Sugar Land, TX (US); Saudi Arabian Oil Company, Dhahran (SA)

(72) Inventors: Simone Di Santo, Dhahran (SA); Wael Abdallah, Dhahran (SA); Shouxiang Mark Ma, Dhahran (SA); Ali Jasim A Al Solial, Dhahran (SA)

(73) Assignees: Schlumberger Technology Corporation, Sugar land, TX (US); Saudi Arabian Oil Company, Dhahran (SA)

( * ) Notice: Subject to any disclaimer, the term of this patent is extended or adjusted under 35 U.S.C. 154(b) by 358 days.

(21) Appl. No.: 18/058,934

(22) Filed: Nov. 28, 2022

(65) Prior Publication Data

US 2024/0175857 A1 May 30, 2024

(51) Int. Cl.
G01N 33/24 (2006.01)
G01N 25/18 (2006.01)
G06N 20/00 (2019.01)

(52) U.S. Cl.
CPC .............. *G01N 33/24* (2013.01); *G01N 25/18* (2013.01); *G06N 20/00* (2019.01)

(58) Field of Classification Search
CPC ......... G01N 33/24; G01N 25/18; G06N 20/00
See application file for complete search history.

(56) References Cited

U.S. PATENT DOCUMENTS

| | | | |
|---|---|---|---|
| 11,215,035 B2 | 1/2022 | Al-Ofi et al. | |
| 2009/0065253 A1 | 3/2009 | Suarez-Rivera | |
| 2010/0000792 A1 | 1/2010 | Alberty | |
| 2011/0061860 A1 | 3/2011 | Dean | |
| 2014/0190691 A1 | 7/2014 | Vinegar | |
| 2014/0208825 A1 | 7/2014 | Holba | |
| 2014/0351183 A1 | 11/2014 | Germain | |
| 2017/0074772 A1 | 3/2017 | Walls | |
| 2025/0052924 A1* | 2/2025 | Craddock | G06N 3/045 |

OTHER PUBLICATIONS

Clark, Jr., S. P., "Thermal Conductivity", Section 21 in Handbook of Physical Constants, Geological Society of America Memoir 97, 1966, 31 pages.

(Continued)

*Primary Examiner* — Walter L Lindsay, Jr.
*Assistant Examiner* — Geoffrey T Evans (57) ABSTRACT

Methods and systems are provided for predicting thermal properties of a subsurface rock formation. A training dataset is derived from petrophysical properties of a plurality of formation rock samples and thermal properties of the plurality of formation rock samples. The training dataset is used to train a machine learning model that predicts label data representing the predefined set of thermal properties given input data representing the predefined set of petrophysical properties of an arbitrary formation rock sample. The machine learning model can be validated and deployed for use in predicting thermal properties of subsurface rock formations.

12 Claims, 6 Drawing Sheets

(56) References Cited

OTHER PUBLICATIONS

Abdallah, W. et al., "Matrix Dielectric Permittivity for Enhanced Formation Evaluation", SPE-204886-MS, presented at the SPE Middle East Oil Gas Show and Conference, Manama, Bahrain, Dec. 2021, 21 pages.

Al-Obaidy, S. H. et al., "Investigation of Thermal Properties of Reservoir Rocks at Different Saturation", International Research Journal of Modernization in Engineering Technology and Science, 2020, 2(12), pp. 13-17.

Beck, A.E., "Techniques of Measuring Heat Flow on Land", in Terrestrial Heat Flow, Lee, W.H.K., ed., American Geophysical Union Monograph No. 8, 1965, p. 24-57.

Beck, J. M. et al., "Computing Thermal Conductivities of Rocks from Chips and Conventional Specimens", Journal of Geophysical Research, 1965, 70(20), pp. 5227-5239.

Birch, F., "Flow of Heat in the Front Range, Colorado", Geological Society of America Bulletin, 1950, v. 61, p. 567-630.

Castiglone, P. et al., "Thermal Conductivity 33, Thermal Expansion 21", proceedings of the 33rd International Thermal Conductivity Conference and the 21st International Thermal Expansion Symposium, 2017, Heng Ban, PH.D (editor), 11 pages.

Diment, W. H. et al., "Thermal Conductivity of Some Rock-Forming Minerals: A Tabulation", U.S. Geological Survey, Open-File Report No. 88-690, 1988, 16 pages.

Fuchs, S. et al., "Evaluation of common mixing models for calculating bulk thermal conductivity of sedimentary rocks: Correction charts and new conversion equations", Geothermics, 2013, 47, pp. 40-52.

Horai, K-I, "Thermal Conductivity of Rock-Forming Minerals", Journal of Geophysical Research, 1971, 76(5), pp. 1278-1308.

Lin, W. et al., "Thermal conductivities, thermal diffusivities, and volumetric heat capacities of core samples obtained from the Japan Trench Fast Drilling Project (JFAST)", Earth, Planets, and Space, 2014, 68, pp. 66, 11 pages.

Robertson, E. C. et al., "Thermal Conductivity of Vesicular Basalt From Hawaii", Journal of Geophysical Research, 1974, 79(32), pp. 4875-4888.

Robertson, C. "Thermal Properties of Rocks. Geological Society of America", Open-File Report 88-441, 1988, 110 pages.

Sass, J. H. et al., "Thermal Conductivity of Rocks from Measurements on Fragments and its Application to Heat-Flow Determinations", Journal of Geophysical Research, 1971, 76(14), pp. 3391-3401.

Valori, A. et al., "Downhole Wettability: The Potential of Nmr", SPE-190332-MS, presented at the 2018 SPE EOR Conference at Oil and Gas West Asia, Muscat, Oman, pp. 1-8.

Zimmerman, R. W., "Thermal Conductivity of Fluid-Saturated Rocks", Journal of Petroleum Science and Engineering, 1989, pp. 219-227.

Ugwu, U. P. et al., "Petrophysical Evaluation for Development of a Marginal Oil Field in the Offshore Niger Delta, Nigeria", Scientia Africana, 2022, pp. 123-132.

1st Substantive Exam Report issued in Saudi Arabian Patent Application No. 122440696 dated Mar. 20, 2025, 29 pages.

\* cited by examiner

METHODS AND SYSTEMS FOR PREDICTING FORMATION THERMAL PROPERTIES

FIELD

The present disclosure relates to methods that characterize thermal properties of subsurface rock formations, such as thermal conductivity, thermal diffusivity and thermal capacity of subsurface rock formations.

BACKGROUND

Thermal properties of rocks have been investigated for decades. For example, techniques for measuring thermal conductivity of rocks have been described by F. Birch, "Flow of heat in the Front Range," Colorado, Geological Society of America Bulletin, v. 61, 1950, p. 567-630; J. M. Beck et al., "Computing thermal conductivities of rocks from chips and conventional specimens," Journal of Geophysical Research, v. 70, 1965, p. 5227-5239; and J. H Sass et al., "Thermal conductivity of rocks from measurements on fragments and its application to heat-flow determinations," Journal of Geophysical Research, v. 76, 1971, p. 3391-3401.

However, there is a wide variation in the thermal properties of subsurface rock formations, which prevents the application of this branch of rock physics to reservoir evaluation workflows. More specifically, subsurface rock formations (also referred to herein as "formations" or "rock formations") are often composed of different mineral components (such as quartz, calcite, etc.) and, in most cases, saturated with one or more fluids (such as water, oil, and/or gas). The mineral components and the fluids have different thermal properties (see Table 1) that contribute to the wide variation in the thermal properties of the rock formations. Nevertheless, thermal properties of rock formations are important physical parameters in many applications such as thermal oil recovery methods (see T. C. Boberg, "Thermal Methods of Oil Recovery," John Wiley, Somerset, N.J., 1988) or geothermal evaluations.

constants," Geological Society of America Memoir 97, 1966, p. 587 describe mineral thermal properties.

Today, the thermal conductivity of subsurface rock formations is estimated by applying these methods. The main, and often the only, input is the rock mineral composition. In some cases, the contribution of fluid is considered as described in Fuchs et al. "Evaluation of common mixing models for calculating bulk thermal conductivity of sedimentary rocks: Correction charts and new conversion equations," Geothermics Vol. 47, 2013, pgs. 40-52. These methods, however, are limited to only one fluid type and do not attempt to consider that case where a mixture of fluids saturate a subsurface rock.

Laboratory experiments conducted on porous rocks filled with air or water have shown a clear correlation between thermal conductivity and quartz abundancy in the matrix. See E C Robertson, "Thermal Properties of Rocks," Geological Society of America, Open-File Report 88-441. 1988. The thermal conduction around pores and through pore fluids in most of the experiments were modelled to create parallel and serial systems which were returning appreciable results in terms of predictability when samples were saturated with single fluids.

In this respect, a relationship between thermal conductivity (k) and solidity ($\gamma$), which is a porosity complement parameter ($\gamma=1-\varphi$), has been observed by many authors. The 1974 paper by E. C. Robertson et al. cited above found a linear relationship between thermal conductivity and the square of the Solidity: $k=f(\gamma^2)$. This effect can be explained with the fact that the solid grains are apparently almost isolated by cracks and contact each other at only a few points.

More recently, experiments have been conducted that estimate the thermal conductivity of fluid-saturated porous rocks as described in R. Zimmerman, "Thermal conductivity of fluid-saturated rocks," Journal of Petroleum Science and Engineering, Vol. 3. 1989, pg. 219-227 and Al-Obaidi et al., "Investigation of Thermal Properties of Reservoir Rocks at Different Saturation," Vol. 2, 2020, pgs. 13-17.

TABLE 1

Thermal properties of minerals and fluids commonly encountered in subsurface rock formations

| Material | Quartz (23° C.) | Sandstone (23° C.) | Calcite (23° C.) | Water (25° C.) | Oil (23° C.) | Gas (1 atm) (23° C.) |
|---|---|---|---|---|---|---|
| k, W/(m · K), thermal conductivity | 1.315 | | | 0.601 | | 0.0264 |
| $\rho$, g/cc, density | 2.65 | 2.42 | 2.71 | 1 | ~0.8 | |
| hc, J/(m$^3$ · K), thermal capacity | 0.94 | | | 4.138 | | 0.0012 |
| K, mm$^2$/s, thermal diffusivity | 1.4 | 1.15 | 1.65 | 0.145 | | 22 |

If the mineral composition, or mode, of a subsurface rock formation can be measured (for example by the LithoScanner tool of SLB of Houston, Texas), several theoretical models can be used to calculate the thermal conductivity of the subsurface rock formation from tables of values for minerals. E. C. Robertson et al., "Thermal conductivity of vesicular basalt from Hawaii," Journal of Geophysical Research, v. 79, 1973, p. 4875-4888 describes models, while Diment et al. "Thermal conductivity of some rock-forming minerals: a tabulation," U.S. Geological Survey, Open-File report 88-690, 1988, K. Horai, "Thermal conductivity of rock-forming minerals. Journal of Geophysical Research, v. 76, 18971, p. 1278-1308, and Clark, "Handbook of physical

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with the subject disclosure, methods and systems are provided for predicting thermal properties of a subsurface rock formation. In embodiments, a training dataset is derived from petrophysical properties of a plurality of formation rock samples and thermal properties of the plurality of formation rock samples. The training dataset is used to train a machine learning (ML) model that predicts label data representing the predefined set of thermal properties given input data representing the predefined set of petrophysical properties of an arbitrary formation rock sample. The ML model can be validated and deployed for use in predicting thermal properties of subsurface rock formations.

In embodiments, the training dataset can be derived from measurements on a plurality of formation rock samples that have i) different lithologies, wettabilities, and fluids with varying saturation fluids and/or ii) varying proportions of reservoir hydrocarbons and formation water and/or iii) fluids with formation water of varying salinity.

In embodiments, the petrophysical properties of the plurality of formation rock samples can be measured by laboratory measurements on the plurality of formation rock samples, and the thermal properties of the plurality of formation rock samples are measured by additional laboratory measurements on the plurality of formation rock samples.

In embodiments, the ML model can include an artificial neural network.

In embodiments, the predefined set of petrophysical properties can be selected from the group consisting of: resistivity, porosity, permeability, grain density, wettability, lithology, dielectric, acoustic properties, nuclear magnetic resonance properties, formation temperature, fluid salinity, and fluid saturations.

In embodiments, the predefined set of thermal properties can be selected from the group consisting of: thermal conductivity, thermal diffusivity, and thermal capacity.

In embodiments, some or all of the operations can be performed by a processor.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

FIG. 1 is a flow chart illustrating an example workflow that employs a trained machine learning model to predict thermal properties of a subsurface rock formation.

Figure 1A:
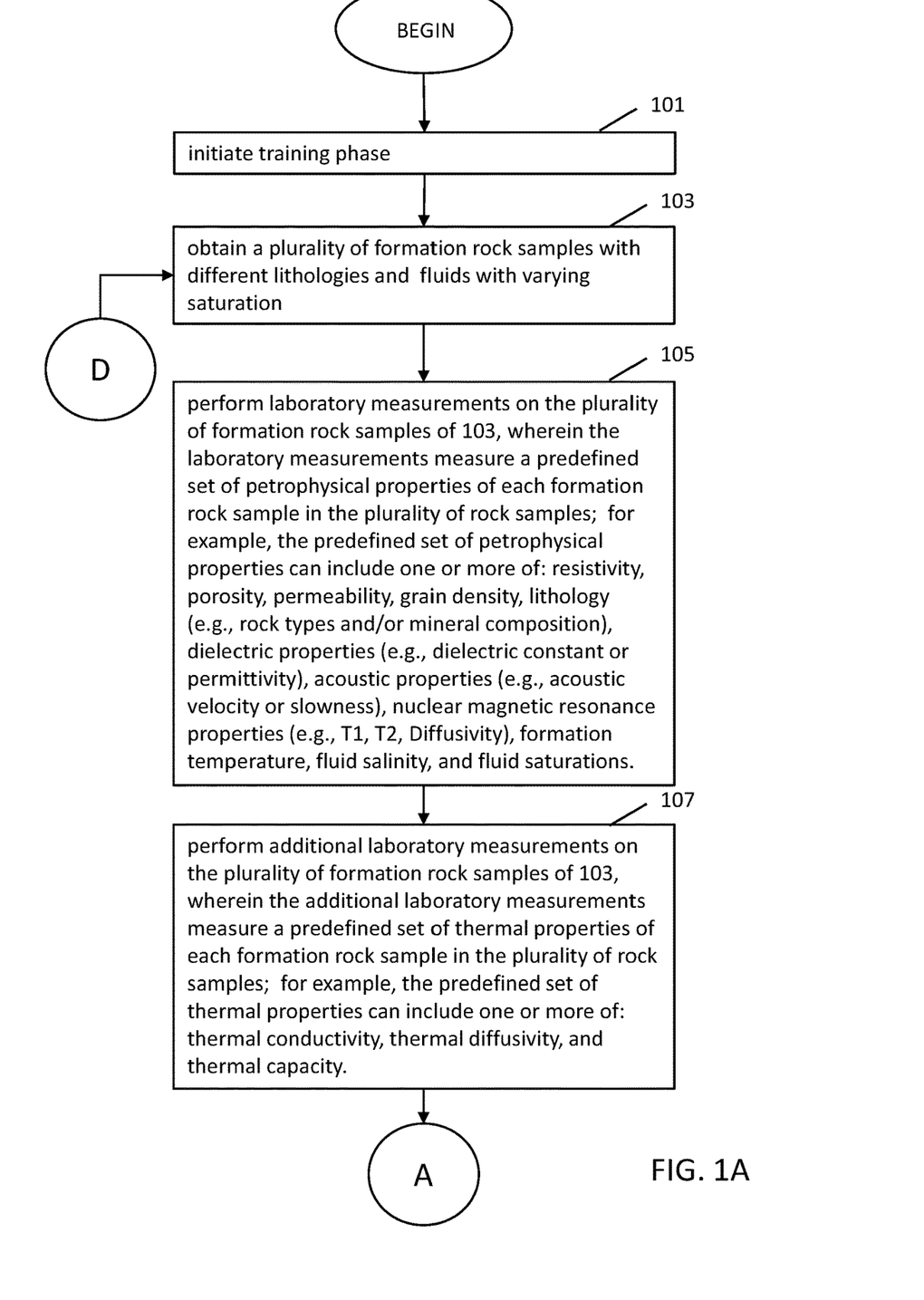
FIGS. 1A to 1D, collectively, is a flow chart illustrating an example workflow that employs a trained machine learning model to predict thermal properties of a subsurface rock formation.

In 101, a training phase is initiated.

In 203, a plurality of formation rock samples are obtained. The formation rock samples have different lithologies (different mineral components), wettabilities, and fluids (e.g., hydrocarbons such as oil and/or gas, and formation water or brine) with varying saturations. The formation rock samples can be core samples taken during or after drilling a wellbore, a core plug, drill cuttings or other suitable rock sample. In embodiments, the formation rock samples can include combinations of reservoir hydrocarbons and formation water with relative proportions that vary over the full spectrum from 100% Water/0% Hydrocarbons to 0% Water/100% Hydrocarbons. The formation water of the rock core samples can also vary in salinity, for example, over the range from 5 ppK fresh water to 250 ppK brine. In embodiments, the plurality of formation rock samples can include combinations of reservoir hydrocarbons and formation water that include 100% Water/0% Hydrocarbons, 66% Water/33% Hydrocarbons, 33% Water/66% Hydrocarbons, and 0% Water/100% Hydrocarbons as well as varying salinity of formation water that includes 5 ppk, 50 ppk, 150 ppk and 250 ppk.

In block 105, laboratory measurements can be performed on the plurality of formation rock samples of 103. The laboratory measurements can measure a predefined set of petrophysical properties of each formation rock sample in the plurality of formation rock samples. For example, the predefined set of petrophysical properties can include one or more of: resistivity, porosity, permeability, grain density, lithology (e.g., rock types and/or mineral composition), wettability, dielectric properties (e.g., dielectric constant or permittivity), acoustic properties (e.g., acoustic velocity or slowness), nuclear magnetic resonance properties (e.g., T1, T2, diffusivity), formation temperature, fluid salinity, and fluid saturations.

In another example, porosity, lithographic properties (such as grain density, mineral distributions), permeability, and/or dielectric constant or dielectric permittivity of a given formation rock sample can be measured by the principles and techniques described in Abdallah et al., "Matrix Dielectric Permittivity for Enhanced Formation Evaluation," SPE-204886-MS, SPE Middle East Oil & Gas Show and Conference, Manama, Bahrain, December 2021. Wettability describes a preference of a solid surface to be in contact with one fluid rather than another. In reservoir rock, the solid surface is composed of mineral grains, and the fluids in the pore space are typically an immiscible combination of water, oil and gas. The balance of forces—surface tensions—controls wettability between the solid and the fluids and the interfacial tension between the fluids. Surface tension results from the natural tendency of molecules at a fluid interface to be at a higher energy state than those in the bulk of a fluid. This tendency creates a reduced concentration of molecules close to the fluid interface, and the fluid molecules are pulled toward the fluid interior, imparting an adhesive force. This force, found at surfaces between immiscible fluids, is surface tension at gas/liquid boundaries and interfacial tension in liquid/liquid boundaries. In porous formation rock saturated with oil and water, "strongly water-wetting" describes one end of a continuum in which the pore surfaces prefer contact with water. A strongly oil-wetting surface prefers contact with oil. Degrees of wetting apply along the continuum, and if the formation rock has no marked preference for one fluid over the other, its condition is termed intermediate wetting or neutral wetting. In many oil-field applications, wettability is considered binary—the rock is either water-wet or oil-wet. This extreme simplification masks the complexity of wetting physics in reservoir rock. Wettability of a core sample can be measured using spontaneous and forced imbibition and centrifuge capillary pressure measurements or other suitable methods. If a core sample imbibes water spontaneously but not oil, it is water-wet; if a sample imbibes oil, it is oil-wet. If the sample imbibes significant amounts of both water and oil, it is mixed-wet.

In yet another example, permeability, dielectric constant or dielectric permittivity and/or acoustic properties (such as acoustic velocity or slowness) of a given formation rock sample can be measured by the principles and techniques described in US Patent No.: U.S. Ser. No. 11/215,035B2.

In still another example, magnetic resonance (MR) properties (such as T1, T2, and Diffusivity) of a given formation rock sample can be measured by the principles and techniques described in Valori et al., "Downhole Wettability: The Potential of NMR," SPE-190332-MS, SPE EOR Conference at Oil and Gas West Asia, Oman, March, 2018.

In 107, additional laboratory measurements can be performed on the plurality of formation rock samples of 103. The additional laboratory measurements can measure a predefined set of thermal properties of each formation rock sample in the plurality of formation rock samples. For example, the predefined set of thermal properties can include one or more of: thermal conductivity, thermal diffusivity, and thermal capacity.

For example, thermal conductivity, specific heat capacity, and/or thermal diffusivity of a given formation rock sample can be measured by the principles and techniques described in Zimmerman, "Thermal conductivity of fluid-saturated rocks," Journal of Petroleum Science and Engineering, Volume 3, Issue 3, 1989, Pages 219-227 and Castiglione et al., "Improved Transient Method Measures Thermal Conductivity of Insulating Materials," 10.12783/tc33-te21/30335, 2017.

Figure 1B:
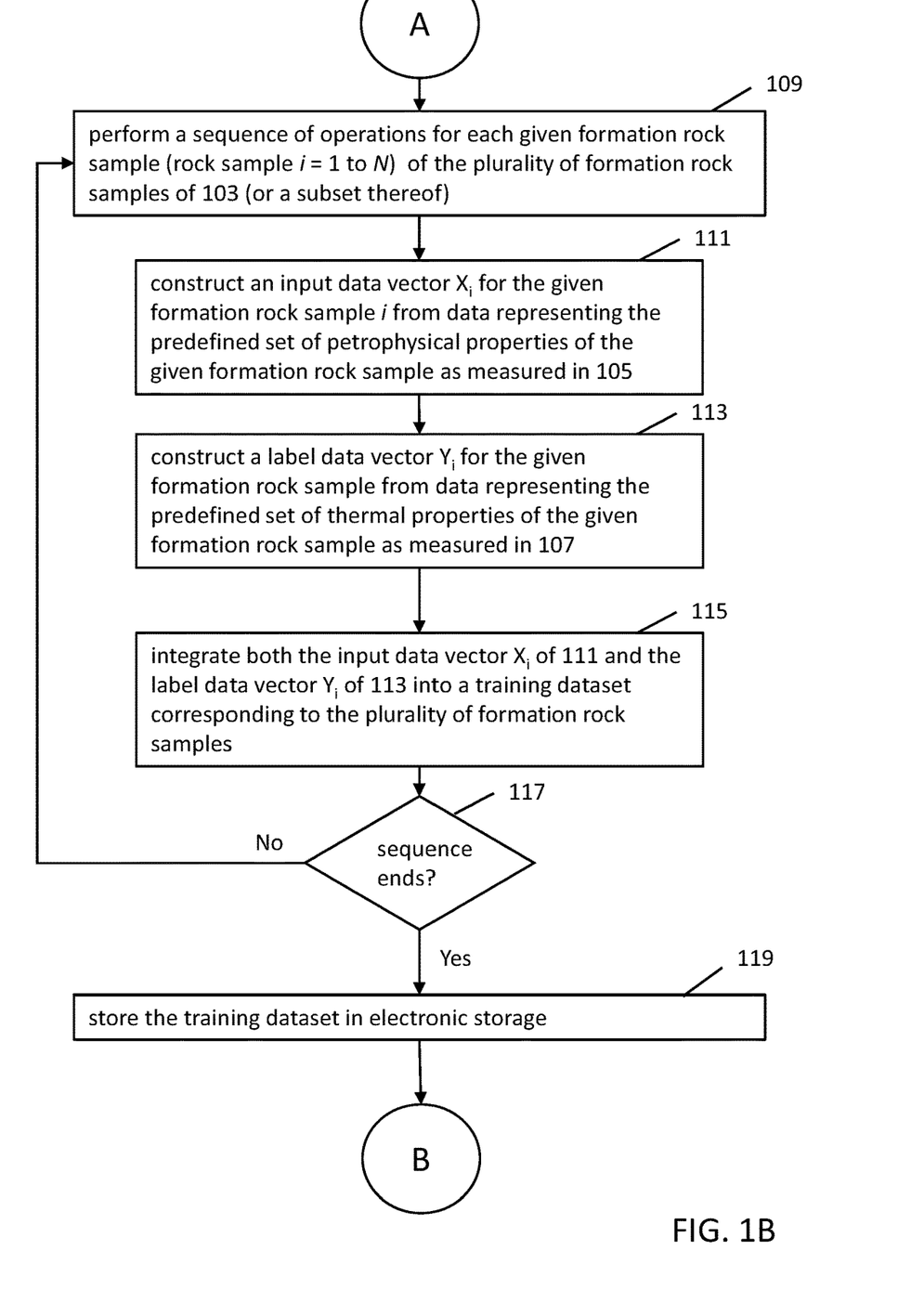

In 109 to 117, a sequence of operations (111 to 115) is performed for each given formation rock sample (rock sample i=1 to N) of the plurality of formation rock samples of 103 (or a subset thereof).

In 111, an input data vector $X_i$ is constructed for the given formation rock sample i from the data representing the predefined set of petrophysical properties of the given formation rock sample as measured in 105.

In 113, a label data vector $Y_i$ is constructed for the given formation rock sample from data representing the predefined set of thermal properties of the given formation rock sample as measured in 107.

In 115, both the input data vector $X_i$ of 111 and the label data vector $Y_i$ of 113 are integrated into a training dataset corresponding to the plurality of formation rock samples.

In 117, after the sequence of operations of 113 to 115 is completed for the number of formation rock samples, the operations continue to 119.

In 119, the resulting training dataset is stored in electronic storage.

Figure 1C:
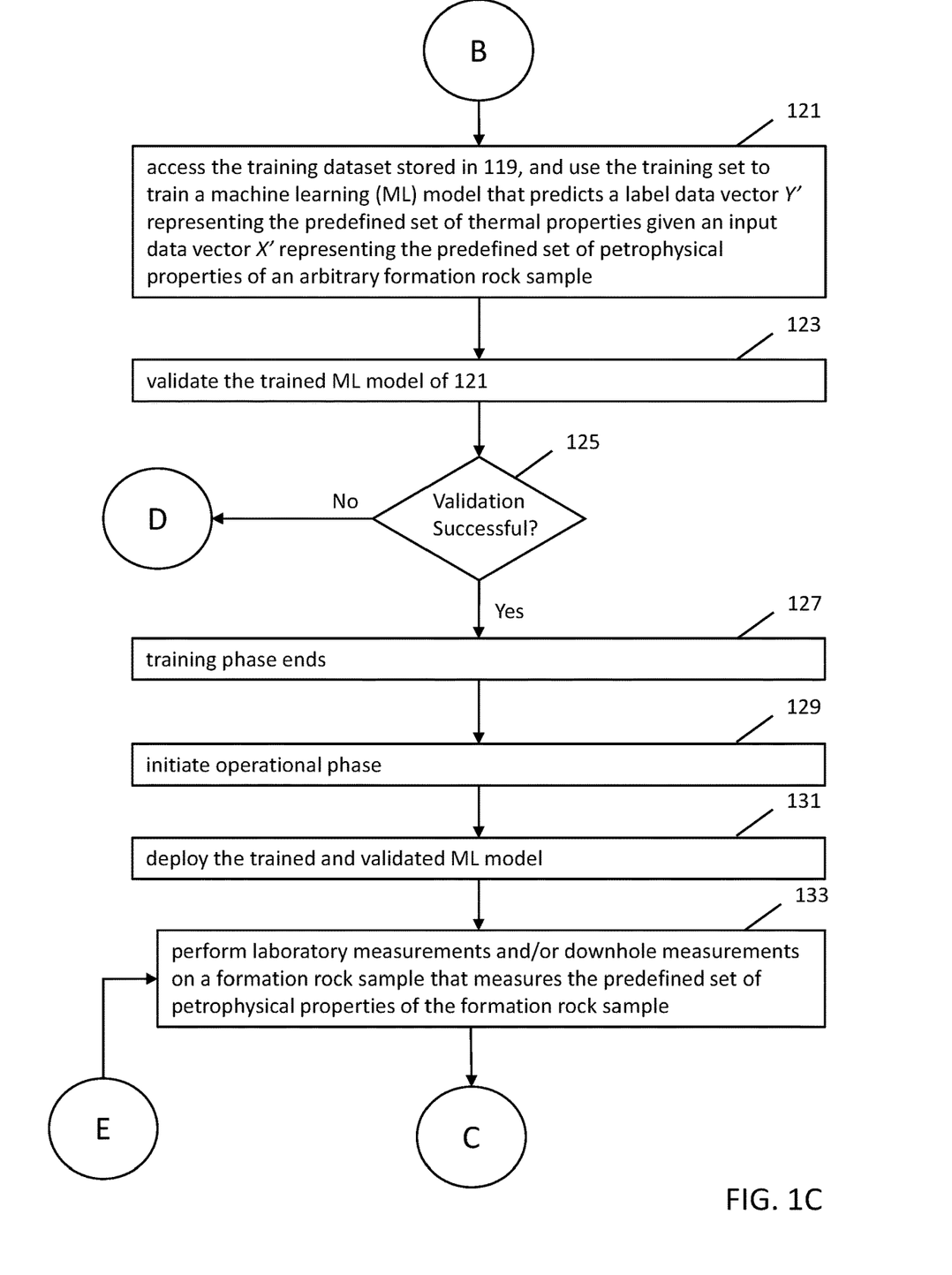

In 121, the training dataset stored in 119 is accessed and used to train a machine learning (ML) model that predicts a label data vector Y' representing the predefined set of thermal properties given an input data vector X' representing the predefined set of petrophysical properties of an arbitrary formation rock sample. In embodiments, the training can employ a supervised learning technique such as regression. The regression-type learning can be used when the output data of the label data vector Y' can have numerical values within one or more predefined ranges. The training can employ one or more scripts to automate tasks as deemed appropriate.

In 123, the trained ML model of 121 is validated. In embodiments, such operations can supply an input data vector $X_y$ representing the predefined set of petrophysical properties of a formation rock sample y to the trained ML model of 121, which outputs a label data vector $Y_y$ representing the predefined set of thermal properties predicted by the ML model for the formation rock sample y given the input data vector $X_y$. The data of the labeled data label data vector $Y_y$ can be compared to corresponding values of known or measured thermal properties for the formation rock sample y and the resulting difference characterizes the accuracy of the ML model. Such operations can be repeated for a number of formation rock samples separate and distinct from the ML model, and the differences for the number of formation rock samples can be evaluated to determine whether the validation of the ML model is successful or not (i.e., whether the ML model is determined to be valid or not valid).

In 125, if the model validation of 123 is successful, the operations continue to 127; otherwise (where the model verification is not successful), the operations of 103 to 123 can be repeated to refine and train the ML model and validate the ML model of 121.

In 127, the training phase ends.

In 129, an operational phase is initiated.

In 131, the trained and validated ML model is deployed for use in predicting thermal properties of formation subsurface rocks.

Figure 1D:
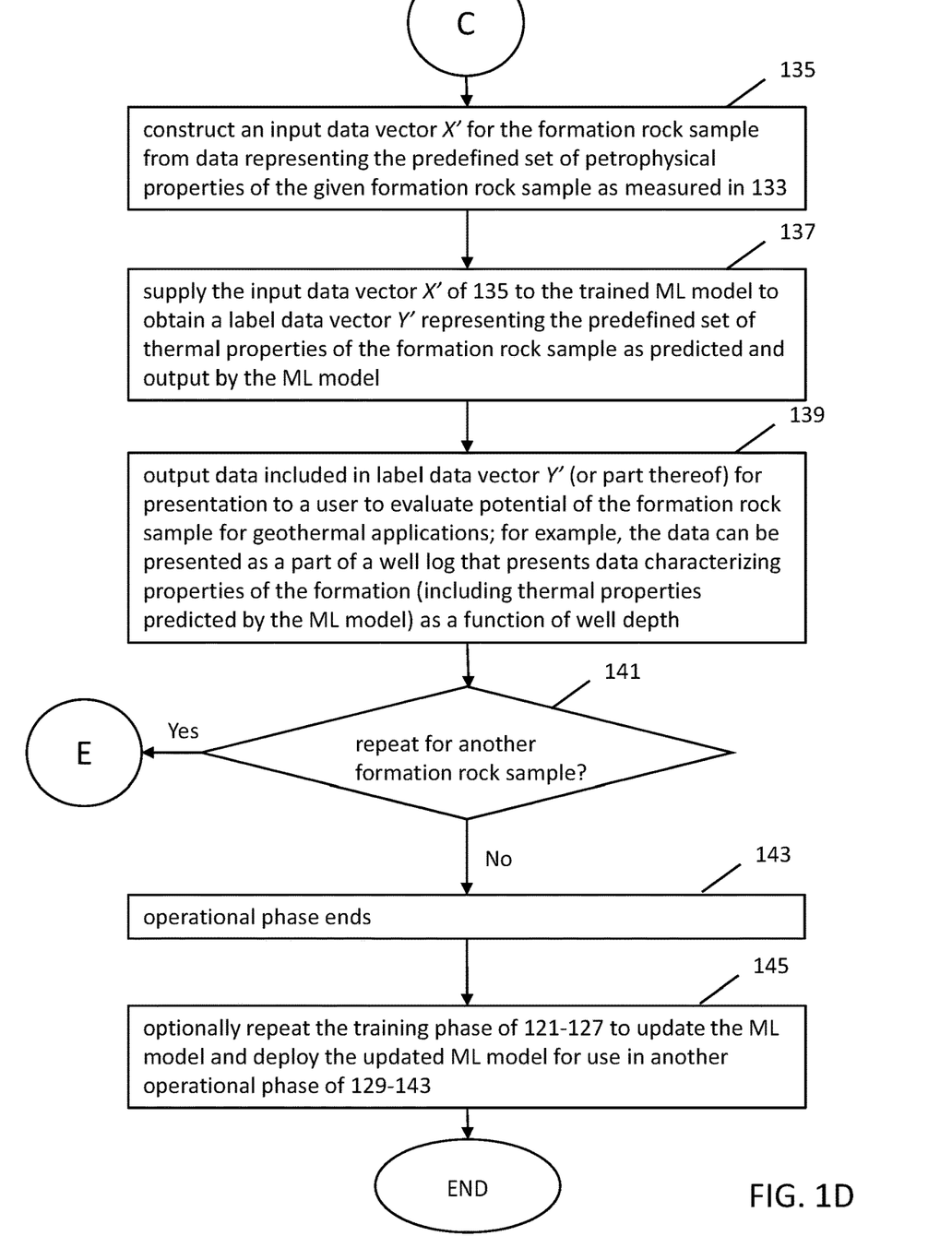

In 133, laboratory measurements and/or downhole measurements can be performed on a formation rock sample that measures the predefined set of petrophysical properties (e.g., one or more of: resistivity, porosity, permeability, grain density, lithology (e.g., rock types and/or mineral composition), wettability, dielectric properties (e.g., dielectric constant or permittivity), acoustic properties (e.g., acoustic velocity or slowness), nuclear magnetic resonance properties (e.g., T1, T2, Diffusivity), and fluid saturations of the formation rock sample. Such measurements can employ principles and techniques similar to those described above with respect to 105. In the case of downhole measurements, one or more downhole tools can be deployed in an open wellbore that traverses formation rock and conveyed to a location at or near the formation rock and operated to perform the relevant measurements during or after drilling the wellbore to measure one or more petrophysical properties of the formation rock. Alternatively, one or more downhole tools can be deployed in a cased wellbore that traverses formation rock and conveyed to a location at or near the formation rock and operated to perform the relevant measurements to measure one or more petrophysical properties of the formation rock. Examples of a variety of such downhole tools that measure the petrophysical properties of the formation rock are commercially available from SLB of Houston, Texas.

In 135, an input data vector X' is constructed for the formation rock sample from data representing the predefined set of petrophysical properties of the given formation rock sample as measured in 133.

In 137, the input data vector X' of 135 is input to the trained ML model to obtain a label data vector Y' representing the predefined set of thermal properties of the given formation rock sample as predicted and output by the trained ML model.

In 139, data included in the label data vector Y' (or part thereof) can be output for presentation to a user to evaluate potential of the formation rock sample for geothermal applications; for example, the data can be presented as a part of a well log that presents data characterizing properties of the formation rock (including thermal properties predicted by the ML model) as a function of well depth. The geothermal applications can include heating and cooling of buildings and industrial facilities, water desalination and electrical power generation, each using geothermal energy as part of the applications.

In 141, the operations check whether the operational phase should continue for analysis of one or more additional formation rock samples. If so, the operations revert back to 135 to repeat the operations of 135 to 141. Otherwise, the operations continue to 143.

In 143, the operational phase ends.

In optional 145, the training phase of 121-127 can be repeated to update the ML model and deploy the updated ML model for use in another operational phase of 129-143.

Figure 2:
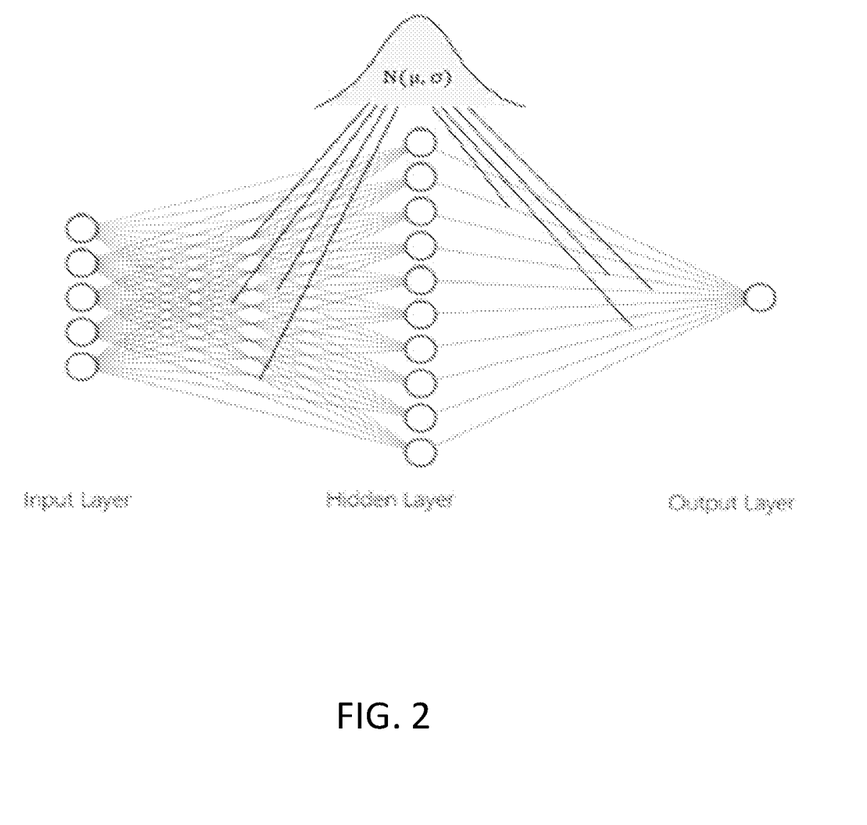
FIG. 2 is a schematic illustration of a ML model that can be used as part of the workflow of FIGS. 1A to 1D.

In embodiments, the ML model of the workflow can be implemented by an artificial neural network (ANN), which is a computational model that includes a collection of layers of nodes interconnected by edges with weights and activation functions associated with the nodes. Input data is applied to one or more input nodes of the ANN and propagate through the ANN in a manner influenced by the weights and activation functions of the nodes, e.g., the output of a node is related to the application of the activation function to the weighted sum of its inputs. As a result, one or more outputs are obtained at corresponding output node(s) of the ANN. The layer(s) of nodes between the input nodes and the output node(s) are referred to as hidden layers, and each successive layer takes the output of the previous layer as input. Parameters of the ANN, including the weights associated with the nodes of the ANN, are learnt during a training phase (or training). FIG. 2 illustrates an example ANN.

Figure 3:
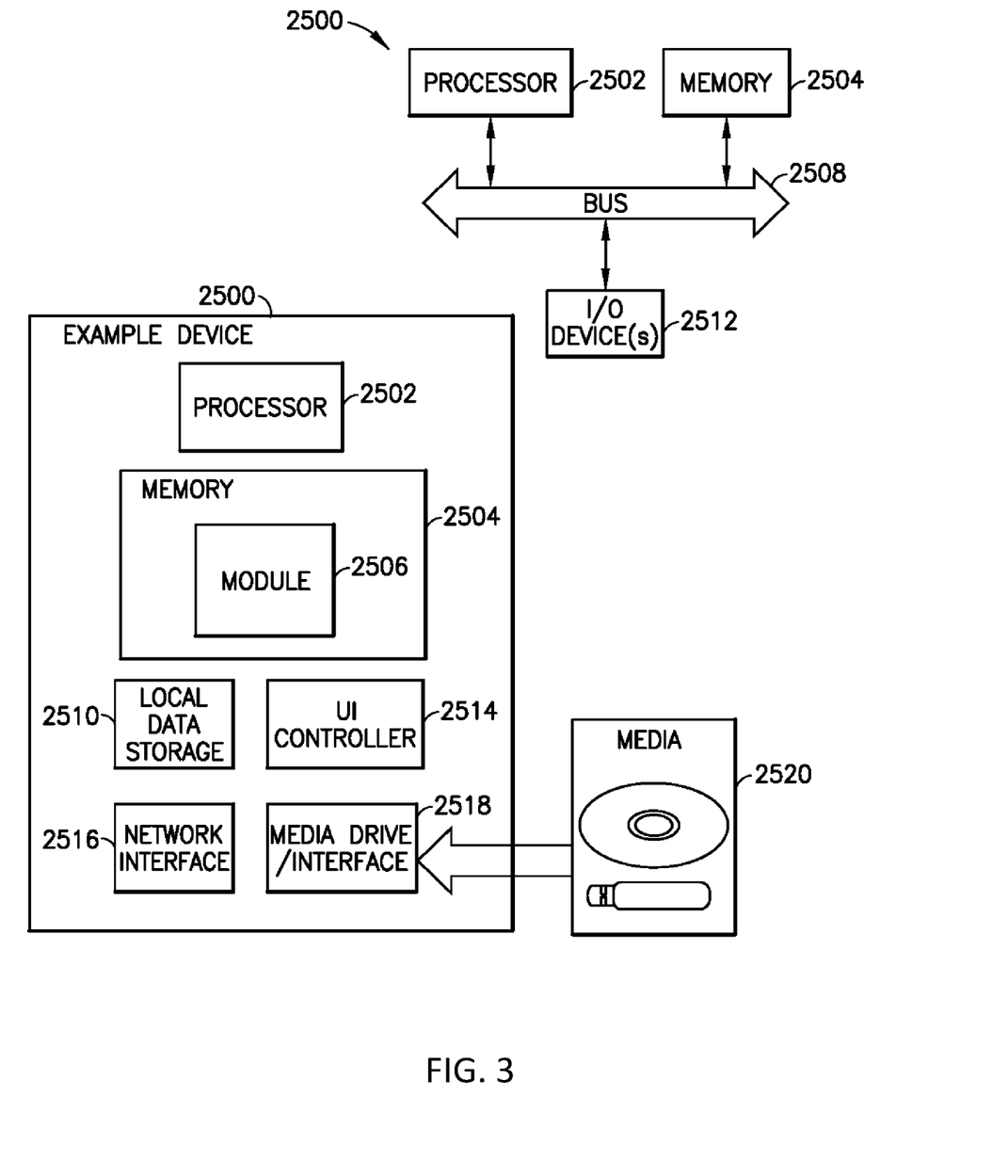
FIG. 3 is a schematic diagram of an example computing system.

In some embodiments, the methods and systems of the present disclosure may involve a computing system. FIG. 3 illustrates an example computing system 2500, with a processor 2502 and memory 2504 that can be configured to implement various embodiments of the subject disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth). One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network. A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user (such as a human annotator) to enter commands and information to device 2500, and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various systems and processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable, and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, general-purpose computer, special-purpose machine, virtual machine, software container, or appliance) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Although only a few example embodiments have been described in detail above, those skilled in the art will readily appreciate that many modifications are possible in the example embodiments without materially departing from this disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claims expressly uses the words 'means for' together with an associated function.

What is claimed is:

1. A method for characterizing thermal properties of a subsurface formation, comprising:
   i) obtaining a plurality of formation rock samples;
   ii) performing laboratory measurements on the plurality of formation rock samples, wherein the laboratory measurements measure a predefined set of petrophysical properties of each formation rock sample in the plurality of formation rock samples;
   iii) performing additional laboratory measurements on the plurality of formation rock samples, wherein the additional laboratory measurements measure a predefined set of thermal properties of each formation rock sample in the plurality of formation rock samples;
   iv) generating and storing a training dataset derived from the petrophysical properties of the plurality of formation rock samples measured in ii) and the thermal properties of the plurality of formation rock samples measured in iii);
   v) using the training dataset of iv) to train a ML model that predicts label data representing the predefined set of thermal properties given input data representing the predefined set of petrophysical properties of an arbitrary formation rock sample;
   vi) validating the ML model trained in v); and
   vii) in the event of successful validation of the ML model in vi), using the ML model to predict label data representing the predefined set of thermal properties for at least one new formation rock sample given input data representing the predefined set of petrophysical properties of the least one new formation rock sample.

2. The method according to claim 1, wherein:
the operations of iv) to vii) are performed by a processor.

3. The method according to claim 1, wherein:
the ML model comprises an artificial neural network.

4. The method according to claim 1, wherein:
the plurality of formation rock samples have different lithologies, wettabilities, and fluids with varying saturation fluids, and/or
the plurality of formation rock samples have varying proportions of reservoir hydrocarbons and formation water; and/or
the plurality of formation rock samples have fluids with formation water of varying salinity.

5. The method according to claim 1, wherein:
the predefined set of petrophysical properties is selected from the group consisting of: resistivity, porosity, permeability, grain density, lithology, wettability, dielectric, acoustic properties, nuclear magnetic resonance properties, formation temperature, fluid salinity, and fluid saturations.

6. The method according to claim 1, wherein:
the predefined set of thermal properties is selected from the group consisting of: thermal conductivity, thermal diffusivity, and thermal capacity.

7. The method according to claim 1, wherein:
the training dataset of iv) include an input data vector and label data vector for a number of formation rock samples, wherein the input data vector includes data that represents the petrophysical properties of a given formation rock sample as measured in ii) and the label data vector includes data that represents the thermal properties of the given formation rock sample as measured in iii).

8. The method according to claim 7, wherein:
the ML model is trained in v) to predict a label data vector representing the predefined set of thermal properties given an input data vector representing the predefined set of petrophysical properties of an arbitrary formation rock sample.

9. The method according to claim 1, wherein:
the ML model is trained in v) using a regression-type supervised learning method.

10. The method according to claim 1, further comprising:
performing laboratory measurements and/or downhole measurements on the at least one new formation rock sample to derive the input data representing the predefined set of petrophysical properties of the least one new formation rock sample.

11. The method according to claim 1, further comprising:
outputting data included in label data for presentation to a user to evaluate potential of the formation rock sample for geothermal applications.

12. The method according to claim 1, further comprising presenting or displaying a well log that includes data characterizing properties of the formation as a function of well depth, wherein the properties include at least one thermal property predicted by the ML model.

* * * * *